(12) United States Patent
Clark et al.

(10) Patent No.: US 12,156,934 B2
(45) Date of Patent: Dec. 3, 2024

(54) COMPOSITION AND METHOD OF TREATING FRAGILE SKIN

(71) Applicant: Ferndale Pharma Group, Inc., Ferndale, MI (US)

(72) Inventors: Stephen W. Clark, Fort Worth, TX (US); David A. Bass, Fort Worth, TX (US)

(73) Assignee: Ferndale Pharma Group, Inc., Ferndale, MI (US)

( * ) Notice: Subject to any disclaimer, the term of this patent is extended or adjusted under 35 U.S.C. 154(b) by 0 days.

(21) Appl. No.: 18/143,151

(22) Filed: May 4, 2023

(65) Prior Publication Data

US 2023/0277437 A1     Sep. 7, 2023

Related U.S. Application Data

(63) Continuation of application No. 17/540,712, filed on Dec. 2, 2021, now Pat. No. 11,660,263, which is a continuation of application No. 16/687,998, filed on Nov. 19, 2019, now abandoned, which is a continuation-in-part of application No. 16/599,508, filed on Oct. 11, 2019, now abandoned, which is a continuation of application No. 15/441,699, filed on Feb. 24, 2017, now abandoned.

(60) Provisional application No. 62/305,652, filed on Mar. 9, 2016.

(51) Int. Cl.

| | | |
|---|---|---|
| *A61K 8/97* | (2017.01) |
| *A61K 8/31* | (2006.01) |
| *A61K 8/34* | (2006.01) |
| *A61K 8/36* | (2006.01) |
| *A61K 8/365* | (2006.01) |
| *A61K 8/37* | (2006.01) |
| *A61K 8/44* | (2006.01) |
| *A61K 8/46* | (2006.01) |
| *A61K 8/49* | (2006.01) |
| *A61K 8/63* | (2006.01) |
| *A61K 8/67* | (2006.01) |
| *A61K 8/68* | (2006.01) |
| *A61K 8/73* | (2006.01) |
| *A61K 8/81* | (2006.01) |
| *A61K 8/86* | (2006.01) |
| *A61K 8/898* | (2006.01) |
| *A61Q 19/00* | (2006.01) |

(52) U.S. Cl.
CPC .............. *A61K 8/97* (2013.01); *A61K 8/31* (2013.01); *A61K 8/342* (2013.01); *A61K 8/345* (2013.01); *A61K 8/361* (2013.01); *A61K 8/365* (2013.01); *A61K 8/37* (2013.01); *A61K 8/375* (2013.01); *A61K 8/442* (2013.01); *A61K 8/463* (2013.01); *A61K 8/4926* (2013.01); *A61K 8/4946* (2013.01); *A61K 8/63* (2013.01); *A61K 8/678* (2013.01); *A61K 8/68* (2013.01); *A61K 8/735* (2013.01); *A61K 8/8158* (2013.01); *A61K 8/86* (2013.01); *A61K 8/898* (2013.01); *A61Q 19/007* (2013.01)

(58) Field of Classification Search
CPC .................................................... A61Q 19/007
See application file for complete search history.

*Primary Examiner* — Qiuwen Mi
(74) *Attorney, Agent, or Firm* — Julie K. Staple; Dinsmore & Shohl LLP

(57) ABSTRACT

The present invention is a composition and method of treatment for fragile skin, skin disorders, and skin conditions in general through topical systematic and periodic application of a formulation that generally may include ingredients such as but not limited to barrier repair ingredients such as but not limited to Skinmimics®, Retinol®, and glycolic acid; humectants such as but not limited to glycerin, propanediol, low and high molecular weight hyaluronic acids; redensifying agents such as but not limited to Timecode®, a lipo amino acid (palmitoyl glycine); and anti-inflammatory/anti-itch ingredients such as but not limited to soybean sterols, Timecode®, SymCalmin®, menthyl lactate, and niacinamide.

1 Claim, No Drawings

COMPOSITION AND METHOD OF TREATING FRAGILE SKIN

CROSS-REFERENCE TO RELATED APPLICATIONS

This application is a continuation of U.S. patent application Ser. No. 17/540,712, filed Dec. 2, 2021, which is a continuation of U.S. patent application Ser. No. 16/687,998, filed on Nov. 19, 2019, now abandoned, which is a continuation-in-part of U.S. patent application Ser. No. 16/599,508, filed on Oct. 11, 2019, now abandoned, which is a continuation of U.S. patent application Ser. No. 15/441,699, filed on Feb. 24, 2017, now abandoned, in which priority is claimed from U.S. Provisional Patent Application Ser. No. 62/305,652 filed on Mar. 9, 2016. Each of the applications listed above is expressly incorporated herein by reference in their entirety.

BACKGROUND OF THE INVENTION

1. Field of the Invention

In general, the present invention is a composition and method of treatment for fragile skin and skin conditions in general. More in particular, the present invention is a systematic and periodic application of a topical formulation that may include ingredients to improve fragile skin such as but not limited 2% Skinmimics® (a unique concentrate of a mixture of skin-identical long chain ceramides, vegetable based cholesterol, and behenic acid), retinol, glycolic acid, sodium hyaluronate, and allantoin.

2. Description of the Prior Art

Mature skin is often prone to dryness due to deficiencies in skin barrier integrity, decline in sebaceous and sweat gland activity, decreased blood flow, and loss of connective tissue. Specifically, mature skin is marked by decreased synthesis of skin barrier lipids, reduced cohesiveness of superficial skin cells, reduction of collagen fibers, and a steady natural decrease in the skin's natural water content. Each of these aspects impact the skin's ability to retain moisture. Additional side effects due to dehydration involve skin tears, allergic reaction, infection, prolonged healing time due to depressed immune response and itch.

The Mayo Clinic characterizes fragile skin as skin that easily tears or breaks. It is a common problem in older adults. As people advance in years, the layers of skin simply thin and become more fragile. However, there are a number of other factors affecting the skin's thickness. Disorders and medications can also contribute to a thinning of the skin. Furthermore, people who have very fragile skin that bruises easily without being on blood thinners or age-related may have one of several genetic conditions that cause skin fragility. The most common cause like this is ehlers danlos syndrome. This is caused by a defect in the production of collagen in the skin and possibly other parts of the body like blood vessels or joints.

It is therefore desirable to provide a new and improved treatment for fragile skin, skin disorders, and skin conditions in general. The above discussed limitations in the prior art is not exhaustive. The current invention provides an inexpensive and effective composition and method of treatment for skin not currently found in the known art.

SUMMARY OF THE INVENTION

In view of the foregoing disadvantages inherent in the known types of compositions and methods of treating fragile skin, skin disorders, and skin conditions in general now present in the prior art, the present invention provides a new and improved effective composition and method of using the same where the prior art fails. As such, the general purpose of the present invention, which will be described subsequently in greater detail, is to provide a new and improved composition and method for the treatment, which has all the advantages of the prior art and none of the disadvantages.

To attain this, the present invention essentially comprises a systematic and periodic application of a topical non-toxic formulation that may include ingredients to improve fragile skin. In a preferred embodiment, the formulation may be a cream generally comprising barrier repair ingredients such as but not limited to Skinmimics®, Retinol®, and glycolic acid; humectants such as but not limited to glycerin, propanediol, low and high molecular weight hyaluronic acids; redensifying agents such as but not limited to Timecode®, a lipo amino acid (palmitoyl glycine); and anti-inflammatory/anti-itch ingredients such as but not limited to soybean sterols, Timecode®, SymCalmin®, menthyl lactate, and niacinamide. The current invention contemplates the formulation may be utilized in a lotion, cream, liquid, gel, and or combinations thereof and provide an advanced and unique approach to the overall treatment and management.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction, arrangement of the components, and amounts thereof set forth in the following description. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception upon which this disclosure is based may readily be utilized as a basis for the designing of other compositions, methods, and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide a new and improved composition and method of treating fragile skin, skin disorders, and skin conditions in general that may be easily and effectively used by those afflicted with the symptoms associated with fragile skin including but not limited to bruising, thin, easily torn skin, and xerosis.

It is a further object of the present invention to provide a new and improved composition and method of treating fragile skin, skin disorders and skin conditions in general that may be an essential element in an ideal treatment regimen to strengthen and heal thin, mature skin, improving its elasticity and thereby protecting it from the side effects previously mentioned.

An even further object of the present invention is to provide a new and improved composition and method of treating fragile skin, skin disorders and skin conditions in general that is susceptible to a low cost of manufacture with regard to ingredients and associated labor of producing same, and, thus accordingly, is then susceptible to low prices of sale to the consuming public thereby making such economically available.

Still another object of the present invention is to provide a new and improved composition and method of treating fragile skin, skin disorders and skin conditions in general, which provides all of the advantages of the prior art, while simultaneously overcoming some of the disadvantages normally associated therewith.

Another object of the present invention is to provide a new and improved composition and method of treating fragile skin, skin disorders, and skin conditions in general that may be used over large areas of skin for those afflicted without or with reduced detrimental side effects.

Yet another object of the present invention is to provide a new and improved composition and method of treating fragile skin, skin disorders and skin conditions in general that is commercially available such that public awareness is garnered and those afflicted will have a viable and readily available treatment.

An even further object of the present invention is to provide a new and improved composition and method of treating fragile skin, skin disorders and skin conditions in general that combines proven ingredients that have already passed F.D.A. approval.

Still another object of the present invention is to provide a new and improved composition and method of treating fragile skin, skin disorders and skin conditions in general that may be utilized in a cream, lotion, liquid, gel and combinations thereof that is non-irritating, fragrance free, and contains no known sensitizing ingredients.

These, together with other objects of the invention, along with the various features of novelty, which characterize the invention, are pointed out with particularity in the claims annexed to and forming a part of this disclosure. For a better understanding of the invention, its operating advantages, and the specific objects attained by its uses, reference should be had to the accompanying descriptive matter in which there are illustrated preferred embodiments of the invention.

DETAILED DESCRIPTION

The present invention may be a formulation utilized as a cream, lotion, liquid, gel, and combinations thereof and may be utilized as a moisturizer in treating the symptoms associated with fragile skin. It is also understood that the following description of said components is not limited to exact percentages, quantities or ingredients and that it is understood equivalent ingredients known in the art may be substituted or added. Furthermore, the current invention may provide a cosmetically pleasing feature with coloring to match the skin tone. The invention may be applied only once or twice per day depending on the severity of symptoms. It is understood that numerous daily applications may be utilized.

In a preferred embodiment, the formulation may be a cream generally comprising barrier repair ingredients such as but not limited to Skinmimics®, Retinol®, and glycolic acid; humectants such as but not limited to glycerin, propanediol, low and high molecular weight hyaluronic acids; redensifying agents such as but not limited to Timecode®, a lipo amino acid (palmitoyl glycine); and anti-inflammatory/anti-itch ingredients such as but not limited to soybean sterols, Timecode®, SymCalmin®, menthyl lactate, and niacinamide.

Barrier Repair

The current invention contemplates use of barrier repair ingredients. The current invention contemplates an intense moisturizer offered in cream form that functions to soothe, hydrate, and protect dry, mature skin. Improvements in skin moisture levels may be achieved via a barrier effect to prevent water from escaping the skin. Skinmimics®, a multi-lamellar concentrate of long chain ceramides, cholesterol, behenic acid and sphingosine, demonstrates a reparative effect on the stratum corneum. Not only do its components reconstitute the skin barrier, but they may also help to stimulate lipid synthesis and epidermal renewal. Skinmimics® is designed for mature skin to help revitalize water management in the epidermis.

Skinmimics® has proven in-vivo benefits in dry mature skin. It revitalizes dry mature skin by optimizing the total epidermal water management system, repairs the skin's own water protection barrier, activates the skin's own water natural moisturizing system (sphingolipids, filaggrin), and increases the glycerol and water transport mechanism (aquaporin-3). It also contains the recently identified cell-signaling Sphingokine® molecules. Skinmimics® was designed to provide mature skin with three important aspects of skin treatment. Those being protection by correction and repair of membrane defects of the stratum corneum lipid barrier, prevention by supplementation of skin's own precursor substances to finally activate the skin lipid synthesis and regeneration by stimulation of epidermal renewal and repair (filaggrin, aquaporin 3).

It is a unique multi-lamellar concentrate based on advanced Ceramide technology and the newly identified Sphingokines®. Skinmimics® is a skin-identical equimolar blend of new and unique long chain Ceramides (including Ceramide EOP, EOS, NS, NP and AP) with a broad distribution of fatty acid side-chains, new vegetal based cholesterol and behenic acid. These three types of lipids, essential for protection benefits, are combined with the unique Sphingokines®, signaling molecules playing a key role in the prevention and regeneration attributes of Skinmimics®.

In addition to Skinmimics®, the invention contemplates use of Retinol® to strengthen and thicken the skin and glycolic acid to enhance cell turnover rates. As the smallest alpha-hydroxy acid, it is believed to have the best penetration into the skin. By weakening the lipid bonds between cells, glycolic acid allows dead skin cells to shed from the skin surface.

Humectants

The current invention contemplates use of humectants. While reinforcing and repairing the skin barrier are essential to hydrate the skin, humectants are also integral to attract and bind water in the epidermis. A combination of glycerin and propanediol is an effective way to improve skin hydration levels. The two work synergistically to provide greater hydration than either could provide alone. A combination of low and high molecular weight Hyaluronic Acids are added to deliver moisture throughout the epidermis. The high molecular weight component imparts a film forming effect and hydrates the outermost layers of the epidermis, while the low molecular weight version is able to penetrate and moisturize the lower layers.

Redensifying Agents

The current invention contemplates use of redensifying agents. Aside from dehydration, mature skin also suffers a loss of connective tissue and overall thinning. Timecode®, a lipo amino acid (palmitoyl glycine), helps to redensify the skin by boosting the synthesis and proper organization of collagen, protecting the connective tissue from enzymatic degradation, improves cellular metabolism and microcirculation, and as an Interleukin-6 inhibitor provides anti-inflammatory properties.

Anti-Inflammatory/Anti-Itch

The current invention contemplates use of anti-inflammatory and or anti-itch ingredients. Dry skin is typically prone to inflammation and itch. Two ingredients previously mentioned for barrier repair and redensifying effects, Soybean Sterols and Timecode®, have shown to be effective at calming the irritation and inflammation associated with dry skin. SymCalmin®, containing avenathramides, exhibits potent anti-histamine activity to calm itch and reduce redness. Menthyl lactate, a derivative of menthol, delivers a cooling sensation to calm itching. Lastly, niacinamide (Vitamin B3) contributes anti-inflammatory and anti-oxidant activity, as well as improves barrier function via stimulation of ceramide production.

In a preferred embodiment, the current invention may include:

| Phase | Ingredient | Code | % | Wt want | Act Wt |
|---|---|---|---|---|---|
| A | Purified Water | C098210 | 70.93 | 1064.02 | 1102 |
|   | Keltrol CG-SFT | C099129 | 0.60 | 9.00 | 9.01 |
|   | Glycerin 99.7% | C037601 | 1.00 | 15.00 | 15.00 |
|   | Versene NA | CO24150 | 0.10 | 1.50 | 1.49 |
|   | Niacinamide | C05651m | 0.50 | 7.50 | 1.52 |
| B | Glycolic Compound 4 | C037690 | 4.00 | 60.00 | 60.00 |
| C | Arlacel 165 | C100350 | 3.00 | 45.00 | 45.09 |
|   | Stearyl Alcohol | C083820 | 1.00 | 15.00 | 15.05 |
|   | White Petrolatum | C060120 | 0.50 | 7.50 | 7.60 |
|   | Tween 60 | C060350 | 1.00 | 15.00 | 15.10 |
|   | Timecode ® | C101280 | 0.75 | 11.25 | 11.26 |
|   | Ceraphyl 368 | C030690 | 1.00 | 15.00 | 15.07 |
|   | Hallstar IPP | C043392 | 1.00 | 15.00 | 15.10 |
|   | Neobee M5 | C011700 | 1.50 | 22.50 | 22.59 |
|   | Sensasil PCA | C059250 | 0.50 | 7.50 | 7.55 |
|   | Simethicone | C083841 | 0.15 | 2.25 | 3.00 |
| D | Vitamin K1 | C060990 | 0.00 | 0.00 | N/A |
|   | Vitamin E Acetate | C091650 | 0.16 | 2.40 | 2.40 |
|   | Retinol ® 50C | C101620 | 0.08 | 1.20 | 1.21 |
|   | Skinmimics ® | C107510 | 5.00 | 75.00 | 75.00 |
|   | Phytotonine | C107490 | 1.00 | 15.00 | 15.00 |
|   | Phyto-Age | CO20460 | 0.03 | 0.38 | .40 |
|   | Pentavitin | C084450 | 1.00 | 15.00 | 15.00 |
|   | SymCalmin ® | C150620 | 0.50 | 7.50 | 7.60 |
|   | Euxyl PE 9010 | C100050 | 1.00 | 15.00 | 15.20 |
| E | Propanediol | C064200 | 1.50 | 22.50 | 22.60 |
|   | Chione Snowfall White | C106670 | 0.20 | 3.00 | 3.20 |
|   | Sepiplus 400 | C101440 | 2.00 | 30.00 | 30.10 |

The current invention further contemplates the steps of 1) combining Phase A ingredients individually in main vessel, mix until smooth and uniform; 2) separately combining Phase B ingredient and heating to 45° C. with mixing; 3) adding Phase B ingredient to Phase A ingredients and heating to 70-75° C. with mixing; 4) mixing together Phase C ingredients and heating to 70-75° C. with mixing; 5) adding Phase C ingredients to Phase A and B ingredients, mixing well while maintaining the temperature at 70-75° C. and mixing until uniform; 6) after mixing as described in step 4, cool the batch to 35-40° C.; 7) blanketing in argon and adding Phase D ingredients individually while protecting from light; 8) protecting from light and under argon, adding Phase E ingredients to the batch; and 9) cooling to room temperature.

It is also contemplated that the invention may comprise Water, Glycolic Acid, Caprylic/Capric Triglyceride, Polyacrylamide, Glyceryl Stearate, PEG-100 Stearate, Glycerin, Ethylhexyl Palmitate, Palmitoyl Glycine, *Cichorium intybus* (chicory) root extract, Allantoin, Retinol, Caprooyl Phytosphingosine, Salicyloyl Phytosphingosine, Caprooyl Sphingosine, Ceramide AP, Ceramide EOP, Ceramide EOS, Ceramide NP, Ceramide NS, Niacinamide, Sodium Hyaluronate, Tocopheryl Acetate, PCA Dimethicone, Cetyl Alcohol, Cholesterol, Disodium EDTA, Ethylhexylglycerin, Phenoxyethanol Stearyl Alcohol, Ceteareth-25, Ammonium Glycolate, Petrolatum, C13-14 Isoparaffin, Laureth-7, Polysorbate 20, Behenic Acid, and so forth.

It is understood that there are two different naming systems currently in use with respect to ceramides. The one principally used until very recently denoted the 9 known primary ceramides present in human tissue as Ceramides 1 through 9 (in ascending order of relative polarity). An older system, known as the "Motta system" has now returned to common usage. The equivalents between the two systems are: Ceramide 1=ceramide EOS, Ceramide 2=ceramide NS, Ceramide 3=Ceramide NP, Ceramide 4=Ceramide EOH, Ceramide 5=ceramide AS, Ceramide 6=ceramide AP, Ceramide 7=ceramide AH, ceramide 8=ceramide NH, and Ceramide 9=ceramide EOP.

It is also contemplated that the invention may comprise by percentage of weight to weight Water 76.36; Niacinamide 0.50; Glycerin 1.00; Disodium EDTA 0.10; Caprylic/Capric Triglyceride 1.50; Phenoxyethanol (and) Ethylhexylglycerin 1.00; PCA Dimethicone 0.50; Sodium Hyaluronate 0.25; SKINMIMICS® 2.00; Stearyl Alcohol 2.50; Caprooyl Phytosphingosine 0.04; Glyceryl Stearate (and) PEG-100 Stearate 2.50; Petrolatum 0.50; Palmitoyl Glycine 1.00; Ethylhexyl Palmitate 1.00; SEPIGEL® 305 3.25; Tocopheryl Acetate 0.05; Allantoin 0.25; Glycolic Acid (and) Ammonium Glycolate 4.00; and VEDERINE® 1.50. It is understood that more and less amounts are contemplated such as less water of 1.00 and more SKIN SKINMIMICS® of 1.00.

In another preferred embodiment, invention may comprise:

| Trade Name | INCI Name | % |
|---|---|---|
| Purified Water | Water | 76.360 |
| Niacinamide, USP | Niacinamide | 0.500 |
| Glycerin 99.7%, USP | Glycerin | 1.000 |
| Versene NA | Disodium EDTA | 0.100 |
| Neobee M5 | Caprylic/Capric Triglyceride | 1.500 |
| Euxyl PE 9010 | Phenoxyethanol (and) Ethylhexylglycerin | 1.000 |
| Sensasil PCA | PCA Dimethicone | 0.500 |
| Hyaluronic Acid 1% | Sodium Hyaluronate | 0.250 |
| Skinmimics ® | Ceteareth-25 (and) Glycerin (and) Cetyl Alcohol (and) Behenic Acid (and) Cholesterol (and) Ceramide NP (and) Ceramide NS (and) Ceramide EOS (and) Ceramide EOP (and) Ceramide AP (and) Caprooyl Phytosphingosine (and) Caprooyl Sphingosine | 2.000 |
| Stearyl Alcohol | Stearyl Alcohol | 2.500 |
| Sphingokine ® NP | Caprooyl Phytosphingosine | 0.040 |
| Arlacel 165 | Glyceryl Stearate (and) PEG-100 | 2.500 |

-continued

| Trade Name | INCI Name | % |
|---|---|---|
| | Stearate | |
| White Petrolatum | Petrolatum | 0.500 |
| Timecode ® | Palmitoyl Glycine | 1.000 |
| Ceraphyl 368 | Ethylhexyl Palmitate | 1.000 |
| Retinol ® 50° C. | Polysorbate 20 (and) Retinol | 0.100 |
| Sepigel 305 | Polyacrylamide (and) C13-14 Isoparaffin (and) laureth-7 | 3.25 |
| Vitamin E Acetate | Tocopheryl Acetate | 0.050 |
| Allantoin | Allantoin | 0.250 |
| Glycolic compound 4.4 | Glycolic Acid (and) Ammonium Glycolate | 4.000 |
| Phytosphingosine SLC | Salicyloyl Phytosphingosine | 0.100 |
| Vederine | Water (and) *Cichorium intybus* (chicory) root extract | 1.500 |

A number of implementations have been described herein. Nevertheless, it will be understood that various modifications may be made. Accordingly, other implementations are within the scope of the following claims. Changes may be made in the combinations, operations, and arrangements of the various parts, elements, and amounts described herein without departing from the spirit and scope of the invention.

The invention claimed is:

1. A cream composition for the treatment of fragile skin in a subject in need thereof, comprising: 1) a barrier repair ingredient selected from the group consisting of: a) a combination of: ceteareth-25 (and) glycerin (and) cetyl alcohol (and) behenic acid (and) cholesterol (and) ceramide NP (and) ceramide NS (and) ceramide EOS (and) Ceramide EOP (and) ceramide AP (and) caprooyl sphingosine; b) retinol; and c) glycolic acid; 2) a humectant selected from the group consisting of: glycerin, propanediol, low molecular weight hyaluronic acids, and high molecular weight hyaluronic acids; 3) a redensifying agent: palmitoyl glycine; and 4) an anti-inflammatory/anti-itch ingredient selected from the group consisting of: soybean sterols, palmitoyl glycine, an avenathramide, menthyl lactate, and niacinamide.

* * * * *